April 6, 1976 A. GROB Plant Pat. 3,856
KALANCHOE PLANT
Filed Sept. 25, 1974
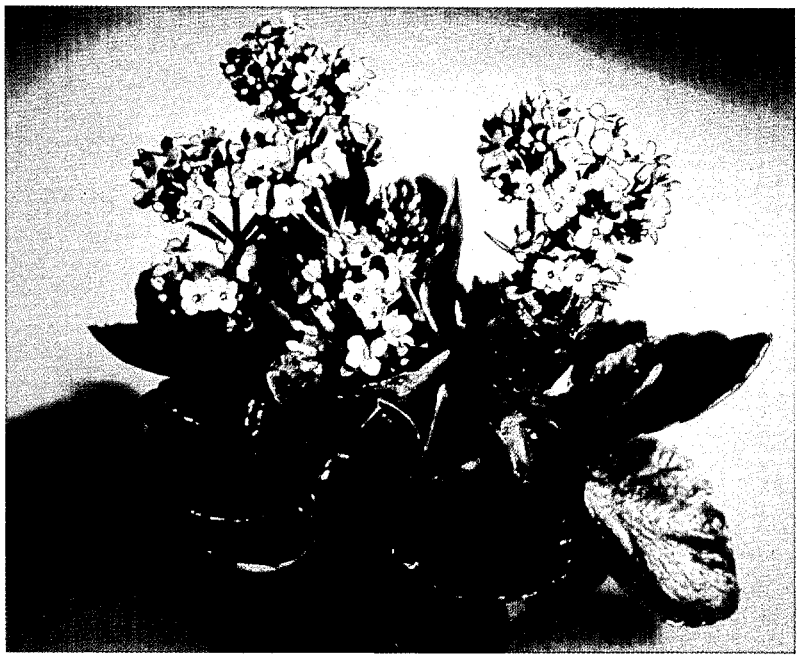

United States Patent

Plant Pat. 3,856
Patented Apr. 6, 1976

3,856

KALANCHOE PLANT

Adolf Grob, St. Gallen, Switzerland, assignor to Mikkelsens Inc., Ashtabula, Ohio

Filed Sept. 25, 1974, Ser. No. 509,144
Int. Cl. A01h *5/00*
U.S. Cl. Plt.—68 1 Claim

The present invention relates to a new and distinct variety of Kalanchoe plant known by the varietal name Kardinal.

The new variety was discovered by me as a selected, cultivated seedling derived from self-crossing of the unpatented Kalanchoe cultivar Grobs Feuerwerk. The new cultivar was discovered by virtue of its unique dark red flower color. The new cultivar was asexually reproduced by vegetative cuttings at St. Gallen, Switzerland, and the unique characteristics of the new cultivar have been transmitted through successive propagations.

The new cultivar is particularly characterized by its very intense dark red colored flowers, its vigorous growth habit and short compact form, and by its wide flower umbels with relatively large petals. The new cultivar is particularly suited for winter flowering under greenhouse culture, with the response period for the new cultivar being 13 weeks in summer and 15 weeks in winter.

With respect to the Kalanchoe cultivar Feuerzauber, disclosed in my copending application Ser. No. 509,143, filed Sept. 25, 1974, perhaps the closest cultivar for comparison purposes, the new cultivar is shorter and more compact in growth, darker red in flower color, has smaller foliage, and is particularly suitable for flowering during the winter season. The new cultivar possesses, to my knowledge, the darkest red flower color available in commerically available Kalanchoes.

The following description is based on plants of the new cultivar initially grown in St. Gallen, Switzerland, and subsequently in Ashtabula, Ohio. Flower color and foliage values are from the RHS Colour Chart.

The accompanying color photographic drawing shows a typical blooming plant of the new cultivar, with the color being as true as possible with color illustrations of this type.

Parentage: The new cultivar is a seedling resulting from self-crossing the parent Grobs Feuerwerk, an unpatented cultivar.

Propagation: By asexually propagating by vegetative cuttings, it has been successfully demonstrated that the new cultivar is stable and produces true to type.

Form: Bush form, semi-dwarf and medium branched.

Growth habit: Medium to dwarf appearance, upright and branching; compact.

Rooting: Normal root growth for kalanchoes.

Blooming habit: Reacts well to short day treatment; can be flowered during the entire year; response period 13 weeks in summer and 15 weeks in winter.

Blooming season: Natural blooming season is January–February although by short day treatment, as noted above, flowering of the cultivar is possible year around.

Foliage: Leaves are opposite, borne at nearly right angles to the stem to 30° above the horizontal; internodal distance is quite short giving a very tight compact appearance.

*Size.*—Similar to cultivars Feuerzauber and Feuerball, measuring approximately 5–7 cm. wide and 7–9 cm. long on mature plants. Feuerball is disclosed in my pending application Ser. No. 509,145, filed Sept. 25, 1974.

*Shape.*—Elliptical in young stages to oval at maturity.

*Texture.*—Smooth, glabrous, crisp, coriaceous.

*Margin.*—Quite crenate when young to repand at maturity.

*Color.*—Upperside, green near 137A approaching maturity to 137C when older. Underside yellow green near 146B.

Disease resistance: Susceptible to powdery mildew.

Flowers:

*Borne.*—On compound terminal paniculate cymes. Main flower stems are heavy and strong even under poor light conditions and short, measuring approximately 7 to 9 cm. below the inflorescence; flower pedicels are short and vigorous, with 8 to 10 or more nodal flowering shoots developing below the main apical inflorescence.

*Quantity.*—Near average for this type of Kalanchoe. Flowering progresses over a period of several months.

*Buds.*—Are full, firm and would be considered large, covered by four light green sepals, measuring approximately 12 to 14 mm. just as the petals begin to emerge.

*Petals.*—Four separate nearly round petals 8 mm., in diameter; total flower diameter 18 to 20 mm., color red 44 AB.

Reproductive organs:

*Stamens.*—Eight, developing in two stages; anthers, light brown, filaments, light yellow to translucent.

*Pollen.*—Light yellow.

*Styles/ovaries.*—Light yellow green, stigmas turn crystalline white with slight purple spotting when receptive; four carpels producing multiple seed.

I claim:

1. A new and distinct cultivar Kalanchoe characterized particularly by its dark red flower color, compact and vigorous growth habit, wide flower umbels with relatively large petals, and by its suitability for flowering during winter season.

No references cited.

ROBERT E. BAGWILL, Primary Examiner